US00PP29401P2

(12) United States Plant Patent
Zaiger et al.

(10) Patent No.: US PP29,401 P2
(45) Date of Patent: Jun. 19, 2018

(54) PEACH TREE NAMED 'SNOW EDEN'

(50) Latin Name: *Prunus persica*
Varietal Denomination: Snow Eden

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days. days.

(21) Appl. No.: 15/530,447

(22) Filed: Jan. 18, 2017

(51) Int. Cl.
*A01H 5/08* (2018.01)

(52) U.S. Cl.
USPC ..... Plt./195

(58) Field of Classification Search
USPC ..... Plt./195, 194
CPC ..... A01H 5/0868; A01H 5/08
See application file for complete search history.

*Primary Examiner* — June Hwu

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium to large size fruit.
3. Clingstone fruit with firm, white flesh.
4. Fruit with good flavor and eating quality.
5. Fruit having an attractive dark red skin color.

1 Drawing Sheet

Botanical designation: *Prunus persica.*
Variety denomination: 'Snow Eden'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sitka' Peach (U.S. Plant Pat. No. 23,799) and the proprietary non-patented peach seedling selections '60ZM590', '13LW44', '43ZN430' and '178LX472'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from a first generation cross between our proprietary non-patented peach seedlings '60ZM590' and '43ZN430'. The seed parent (60ZM590) originated as an open pollinated seedling from our proprietary non-patented peach seedling '13LW44'. The pollen parent (43ZN430) originated as an open pollinated seedling selection from our proprietary non-patented peach seedling '178LX472'. A large number of these first generation crosses were budded to older trees of 'Nemaguard' Rootstock (non-patented) to accelerate rapid fruit production. Under close and careful observation we recognized the desirable tree and fruit characteristics of the present seedling and selected it in 2013 for additional asexual propagation and commercialization.

ASEXUAL REPRODUCTION OF THE VARIETY

In 2013 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of medium to large size, white flesh, clingstone fruit with good flavor and eating quality. The fruit is further characterized by having firm flesh and an attractive dark red skin color. In comparison to its proprietary non-patented peach seed parent '60ZM590' the fruit of the new variety has white flesh compared to yellow flesh and is approximately 10 days earlier in maturity. In comparison to its proprietary non-patented peach pollen parent '43ZN430' the fruit of the new variety is larger in size and is approximately 6 days later in maturity. In comparison to the commercial variety 'Sitka' Peach (U.S. Plant Pat. No. 23,799) the fruit of the new variety is approximately 2 weeks earlier in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 3 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 3 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 2 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 550 hours at or below 45° F.

Trunk:

*Size*.—Medium, average circumference 43.3 cm at 22.9 cm above ground on a 3 year old tree.

*Stocky*.—Medium stocky.

*Texture*.—Medium shaggy, roughness increases with age.

*Color*.—Varies from 5Y 2/2 to 5YR 2/4.

Branches:

*Size*.—Medium. Average circumference 10.4 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 24 in a 25.8 square cm area. Average length 5.1 mm. Average width 2.6 mm. Color varies from 10YR 6/10 to 5YR 6/10.

*Color*.—New growth varies from 5GY 6/6 to 2.5GY 6/6. Mature growth varies from 5YR 3/6 to 7.5YR 3/6, varies with age of growth.

Leaves:

*Size*.—Medium to large. Average length 142.4 mm. Average width 38.2 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 9.6 mm. Average width 1.3 mm. Longitudinally grooved. Surface — glabrous. Color varies from 5GY 4/4 to 5GY 3/4.

*Glands*.—Type — reniform. Size — large. Average length 1.7 mm. Average diameter 1.0 mm. Average number 2, varies from 1 to 3. Located primarily on the base of leaf blade and upper portion of petiole. Color varies from 5GY 4/4 to 7.5GY 5/6.

*Stipules*.—Average number 2. Average length 10.8 mm. Edges — pectinate. Color varies from 7.5GY 5/6 to 5GY 4/6.

*Color*.—Upper surface varies from 2.5GY 3/4 to 5GY 3/4. Lower surface varies from 2.5GY 3/4 to 5GY 4/4. Midvein color varies from 10Y 7/4 to 2.5GY 7/4.

Flower buds:

*Size*.—Large. Average length 20.8 mm. Average diameter 11.9 mm.

*Hardiness*.—Hardy with respect to California winters.

*Density*.—Dense.

*Form*.—Conical, becoming elongated just before opening.

*Pedicel*.—Medium. Average length 5.7 mm. Average width 1.2 mm. Surface — glabrous. Color varies from 5GY 5/6 to 5GY 5/8.

*Color*.—Varies from 5RP 7/8 to 7.5RP 7/8, color fades with age.

Flowers:

*Blooming period*.—Date of First Bloom Feb. 9, 2016. Date of Petal Fall Feb. 19, 2016, varies slightly with climatic conditions.

*Size*.—Large, showy. Average height 21.5 mm. Average diameter 51.4 mm.

*Petals*.—Normally 5, alternately arranged to sepals. Size — large. Average length 23.3 mm. Average width 21.7 mm. Form — obovate. Petal apex — rounded. Petal base — truncate. Margin — sinuate. Arrangement — overlapping. Both upper and lower surfaces glabrous. Color varies from 5RP 8/4 to 5RP 7/6, fades with age of flower.

*Sepals*.—Normally 5, alternately arranged to flowers. Size — large. Average length 7.0 mm. Average width 6.6 mm. Shape — triangular. Apex — rounded to triangular. Margin — entire. Color — upper surface varies from 5GY 5/6 to 5R 2/4. Lower surface varies from 2.5R 3/2 to 5R 2/4. Surface — upper surface glabrous, lower surface pubescent.

*Stamens*.—Average number per flower 47. Average filament length 15.9 mm. On average, the stamens are above the height of the petals. Filament color varies from N 9.5/(white) to 5RP 9/2. Anther color varies from 5R 3/10 to 7.5R 3/8.

*Pollen*.—Self fertile. Color varies from 2.5Y 7/12 to 2.5Y 6/10.

*Pistil*.—Number — normally one. Average length 19.0 mm. Position of stigma an average of 1.0 mm below anthers. Surface — pubescent. Color varies from 10Y 7/6 to 2.5GY 7/6.

*Fragrance*.—Moderate.

*Color*.—Varies from 5RP 8/4 to 5RP 7/6.

*Pedicel*.—Average length 5.1 mm. Average width 1.7 mm. Color varies from 2.5GY 5/8 to 5GY 5/6. Surface — glabrous.

*Number flowers per flower bud*.—Normally one.

Fruit:

*Maturity when described*.—Firm ripe and ready for consumption.

*Date of first picking*.—May 16, 2016.

*Date of last picking*.—May 26, 2016, varies slightly with climatic conditions.

*Size*.—Medium to large. Average diameter axially 59.2 mm. Average transversely in suture plane 65.0 mm. Average weight 161.9 grams, varies slightly with fertility of the soil, amount of thinning and climatic conditions.

*Form*.—Globose.

*Suture*.—Slightly lipped.

*Ventral surface*.—Slightly lipped.

*Apex*.—Slightly retuse.

*Base*.—Retuse.

*Stem cavity*.—Rounded to slightly elongated in suture plane. Average depth 6.3 mm. Average diameter 8.2 mm.

Stem:

*Size*.—Medium. Average length 11.8 mm. Average diameter 3.5 mm.

*Color*.—Varies from 5GY 6/6 to 5GY 5/6.

Flesh:

*Ripens*.—Evenly.

*Texture*.—Firm, meaty.

*Fibers*.—Few, small, tender.

*Firmness*.—Good, comparable to other commercial peach varieties.

*Aroma*.—Slight.

*Amydgalin*.—Undetected.

*Eating quality*.—Good.

*Flavor*.—Good, mild, sweet, sub-acid flavor.

*Juice*.—Moderate amount, enhances flavor.

*Acidity*.—Not available.

*Brix*.—Average Brix 14.0°, varies slightly with amount of fruit per tree and climatic conditions.

*Color*.—Varies from N 9.5/(white) to 5Y 9/2.

*Pit cavity*.—Average length 33.3 mm. Average width 25.2 mm. Average depth 9.9 mm. Color varies from 10Y 8/4 to 10Y 7/4.

Skin:

*Thickness*.—Medium.

*Surface*.—Smooth.

*Pubescence*.—Moderate amount, short in length.

*Tendency to crack*.—None.

*Color*.—Ground color varies from 5Y 8.5/2 to 7.5Y 9/2. Overspread with 7.5R 3/6 to 10R 3/6.

*Tenacity*.—Tenacious to flesh.

*Astringency*.—None.

Stone:

*Type*.—Clingstone, strong adherence to flesh.

*Size*.—Large. Average length 32.2 mm. Average width 24.9 mm. Average thickness 19.7 mm.

*Form*.—Obovoid.

*Base*.—Flat.

*Apex*.—Rounded.

*Surface*.—Pitted throughout, pits vary from round to elongated.

*Sides*.—Unequal, one side extending further outward from suture plane.

*Ridges*.—Small, narrow ridges extending from base toward apex.

*Tendency to split*.—None to very slight.

*Color*.—Varies from 7.5YR 8/4 to 10YR 7/4 when dry.

Kernel:

*Size*.—Medium. Average length 16.7 mm. Average width 10.2 mm. Average depth 6.2 mm.

*Form*.—Ovoid.

*Viability*.—Partially viable, incomplete embryo development.

*Skin color*.—Varies from 5Y 9/2 to 5Y 9/4.

Use: Dessert. Market — local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

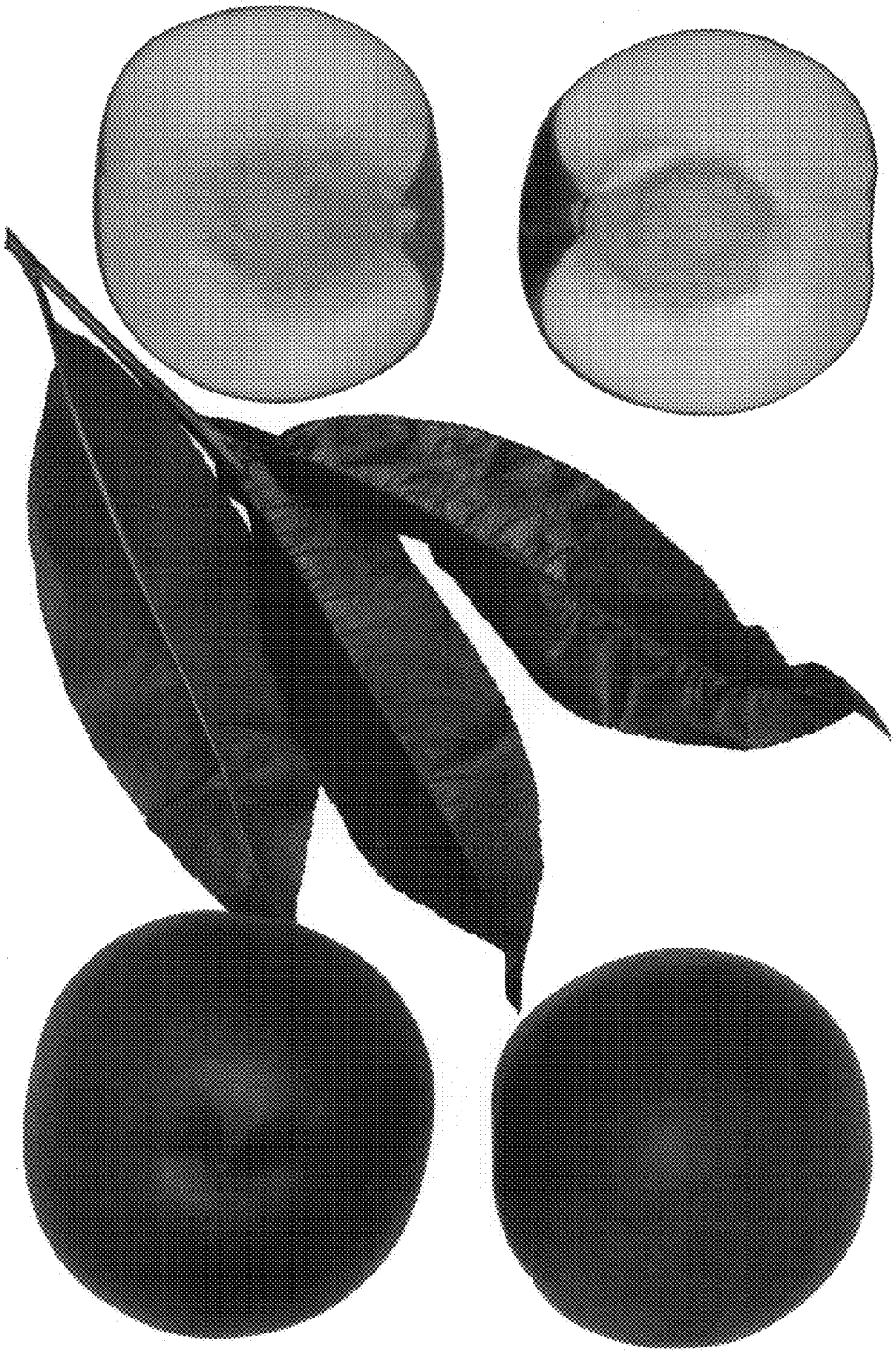

* * * * *